United States Patent
Freudiger et al.

(10) Patent No.: US 10,695,097 B2
(45) Date of Patent: Jun. 30, 2020

(54) ELASTIC ROD HAVING DIFFERENT DEGREES OF STIFFNESS FOR THE SURGICAL TREATMENT OF THE SPINE

(71) Applicants: Stefan Freudiger, Bremgarten (CH); Rolf Diener, Winkel (CH)

(72) Inventors: Stefan Freudiger, Bremgarten (CH); Rolf Diener, Winkel (CH)

(73) Assignee: SPINESAVE AG (CH)

( * ) Notice: Subject to any disclaimer, the term of this patent is extended or adjusted under 35 U.S.C. 154(b) by 0 days.

(21) Appl. No.: 14/408,247

(22) PCT Filed: Jun. 24, 2013

(86) PCT No.: PCT/CH2013/000112
§ 371 (c)(1),
(2) Date: Dec. 15, 2014

(87) PCT Pub. No.: WO2014/005236
PCT Pub. Date: Jan. 9, 2014

(65) Prior Publication Data
US 2015/0173799 A1    Jun. 25, 2015

(30) Foreign Application Priority Data
Jul. 5, 2012   (CH) ..................... 1048/12

(51) Int. Cl.
*A61B 17/70*   (2006.01)
*A61B 17/00*   (2006.01)

(52) U.S. Cl.
CPC ........ *A61B 17/7002* (2013.01); *A61B 17/701* (2013.01); *A61B 17/7031* (2013.01); *A61B 2017/00526* (2013.01)

(58) Field of Classification Search
CPC .... A61B 17/7019–7031; A61B 17/705; B29L 2031/06; B29L 2031/7532; B29L 2031/753; B29C 66/301; B29C 66/20
(Continued)

(56) References Cited

U.S. PATENT DOCUMENTS 5,215,246 A * 6/1993 Thompson ........... B23D 45/044
                                                                     228/13
5,217,461 A * 6/1993 Asher et al. .................. 606/261
(Continued)

FOREIGN PATENT DOCUMENTS

CH         702 636 A1    8/2011
CH         702637 A1 *   8/2011   ......... A61B 17/7011
(Continued)

OTHER PUBLICATIONS

International Preliminary Report on Patentability and the Written Opinion of the International Searching Authority dated Jan. 6, 2015 issued in corresponding International Patent Application No. PCT/CH2013/000112.
(Continued)

*Primary Examiner* — Jacqueline T Johanas
*Assistant Examiner* — Michelle C Eckman
(74) *Attorney, Agent, or Firm* — Ostrolenk Faber LLP

(57) ABSTRACT

For a differentiated treatment of individual motion segments of the spine, a plastic rod (41, 42, 46) for the dynamic stabilization of the spine has different degrees of stiffness in its longitudinal direction. The different rod segments are interconnected along an oblique plane (13).

16 Claims, 2 Drawing Sheets

(58) Field of Classification Search
USPC .......... 606/254–262; 156/304.5, 304.6, 159
See application file for complete search history.

(56) References Cited

U.S. PATENT DOCUMENTS

| | | | | |
|---|---|---|---|---|
| 5,593,408 | A * | 1/1997 | Gayet et al. | 606/261 |
| 6,099,528 | A * | 8/2000 | Saurat | 606/254 |
| 6,197,015 | B1 * | 3/2001 | Wilson | A61M 25/005 |
| | | | | 156/158 |
| 7,815,663 | B2 * | 10/2010 | Trieu | 606/254 |
| 8,038,818 | B2 * | 10/2011 | Murata | G03D 15/04 |
| | | | | 156/137 |
| 8,409,396 | B2 * | 4/2013 | Bech | B29C 66/73941 |
| | | | | 156/304.5 |
| 8,974,497 | B2 * | 3/2015 | Cho et al. | 606/255 |
| 2004/0002708 | A1 * | 1/2004 | Ritland | 606/61 |
| 2005/0203513 | A1 | 9/2005 | Jahng et al. | |
| 2005/0261686 | A1 * | 11/2005 | Paul | 606/61 |
| 2006/0009768 | A1 * | 1/2006 | Ritland | 606/61 |
| 2006/0041259 | A1 | 2/2006 | Paul et al. | |
| 2006/0095134 | A1 | 5/2006 | Trieu et al. | |
| 2006/0142760 | A1 * | 6/2006 | McDonnell | 606/61 |
| 2006/0242813 | A1 * | 11/2006 | Molz et al. | 29/284 |
| 2006/0247638 | A1 * | 11/2006 | Trieu et al. | 606/69 |
| 2007/0005063 | A1 * | 1/2007 | Bruneau et al. | 606/61 |
| 2007/0129729 | A1 * | 6/2007 | Petit et al. | 606/61 |
| 2007/0186990 | A1 * | 8/2007 | Serbousek | 138/135 |
| 2007/0191841 | A1 * | 8/2007 | Justis et al. | 606/61 |
| 2007/0233073 | A1 * | 10/2007 | Wisnewski et al. | 606/61 |
| 2007/0270819 | A1 * | 11/2007 | Justis et al. | 606/61 |
| 2007/0270843 | A1 * | 11/2007 | Matthis et al. | 606/61 |
| 2008/0086127 | A1 * | 4/2008 | Patterson | A61B 17/701 |
| | | | | 606/86 R |
| 2008/0140133 | A1 * | 6/2008 | Allard et al. | 606/308 |
| 2008/0177388 | A1 * | 7/2008 | Patterson | A61B 17/7031 |
| | | | | 623/17.16 |
| 2008/0221620 | A1 * | 9/2008 | Krause | 606/255 |
| 2008/0262548 | A1 * | 10/2008 | Lange et al. | 606/256 |
| 2008/0306536 | A1 | 12/2008 | Frigg et al. | |
| 2008/0312694 | A1 * | 12/2008 | Peterman et al. | 606/257 |
| 2008/0319486 | A1 | 12/2008 | Hestad et al. | |
| 2009/0240284 | A1 * | 9/2009 | Randol et al. | 606/254 |
| 2009/0248077 | A1 * | 10/2009 | Johns | 606/246 |
| 2009/0248083 | A1 * | 10/2009 | Patterson et al. | 606/279 |
| 2009/0270921 | A1 * | 10/2009 | Krause | 606/254 |
| 2009/0270922 | A1 * | 10/2009 | Biedermann | A61B 17/7031 |
| | | | | 606/262 |
| 2009/0287251 | A1 * | 11/2009 | Bae et al. | 606/254 |
| 2010/0042154 | A1 * | 2/2010 | Biedermann et al. | 606/254 |
| 2010/0114165 | A1 * | 5/2010 | Ely | 606/246 |
| 2010/0114167 | A1 * | 5/2010 | Wilcox | A61B 17/7004 |
| | | | | 606/250 |
| 2010/0126654 | A1 * | 5/2010 | Katayama | B29C 65/02 |
| | | | | 156/159 |
| 2010/0217326 | A1 * | 8/2010 | Bowden et al. | 606/279 |
| 2010/0324600 | A1 * | 12/2010 | Biyani | 606/264 |
| 2011/0029018 | A1 * | 2/2011 | Carlos | 606/246 |
| 2011/0054535 | A1 * | 3/2011 | Gephart et al. | 606/259 |
| 2011/0106162 | A1 * | 5/2011 | Ballard et al. | 606/254 |
| 2011/0152936 | A1 * | 6/2011 | Gil et al. | 606/259 |
| 2011/0152937 | A1 * | 6/2011 | Trieu | 606/264 |
| 2012/0065687 | A1 * | 3/2012 | Ballard et al. | 606/259 |
| 2012/0071928 | A1 * | 3/2012 | Jackson | 606/257 |
| 2012/0089188 | A1 * | 4/2012 | Jackson | 606/254 |
| 2012/0112422 | A1 * | 5/2012 | Larsson | B31F 7/004 |
| | | | | 277/631 |
| 2012/0290013 | A1 * | 11/2012 | Simonson | 606/279 |
| 2013/0012997 | A1 * | 1/2013 | Hestad et al. | 606/264 |
| 2013/0079825 | A1 * | 3/2013 | Loke et al. | 606/259 |
| 2013/0103090 | A1 * | 4/2013 | Prevost | 606/254 |
| 2013/0110169 | A1 * | 5/2013 | Hynes et al. | 606/254 |
| 2013/0123855 | A1 * | 5/2013 | Clark | A61B 17/705 |
| | | | | 606/264 |
| 2013/0158606 | A1 * | 6/2013 | Freudiger et al. | 606/264 |
| 2013/0211454 | A1 * | 8/2013 | Beger et al. | 606/255 |
| 2014/0025116 | A1 * | 1/2014 | Wei | 606/255 |
| 2014/0081333 | A1 * | 3/2014 | Jackson | 606/257 |
| 2014/0257393 | A1 * | 9/2014 | Trieu et al. | 606/254 |
| 2015/0039034 | A1 * | 2/2015 | Frankel et al. | 606/261 |
| 2015/0080955 | A1 * | 3/2015 | Celmerowski et al. | 606/254 |
| 2015/0297265 | A1 * | 10/2015 | Arena | A61B 17/7016 |
| 2015/0305779 | A1 * | 10/2015 | Montavon | A61B 17/7028 |
| 2015/0313642 | A1 * | 11/2015 | Fessler | A61B 17/7014 |
| 2017/0105764 | A1 * | 4/2017 | Williams | A61B 17/705 |
| 2017/0135728 | A1 * | 5/2017 | Williams | A61B 17/705 |
| 2019/0142469 | A1 * | 5/2019 | Williams | A61B 17/705 |

FOREIGN PATENT DOCUMENTS

| | | | | |
|---|---|---|---|---|
| CH | 702637 A1 * | 8/2011 | ........ | A61B 17/7011 |
| CH | 703 000 A2 | 10/2011 | | |
| EP | 2 113 216 | 11/2009 | | |
| WO | WO 97/32533 | 9/1997 | | |
| WO | WO 2007/038429 | 4/2007 | | |

OTHER PUBLICATIONS

International Search Report dated Aug. 6, 2013 issued in corresponding International patent application No. PCT/CH2013/000112.

* cited by examiner

ELASTIC ROD HAVING DIFFERENT DEGREES OF STIFFNESS FOR THE SURGICAL TREATMENT OF THE SPINE

CROSS REFERENCE TO RELATED APPLICATIONS

The present application is a 35 U.S.C. § 371 National Phase conversion of PCT/EP2013/000112, filed Jun. 24, 2013, which claims benefit of Swiss patent application no. 1048/12, filed Jul. 5, 2012, the disclosure of which is incorporated herein by reference. The PCT International Application was published in the English language.

TECHNICAL FIELD OF THE INVENTION

The present invention relates to an elastic connecting rod for surgical treatment of the spine, the rod having different degrees of stiffness along its longitudinal axis according to the preamble of claim 1.

BACKGROUND OF THE INVENTION

Elastic connecting rods are typically used in conjunction with pedicle screws for the dynamic stabilization of the spine. If such a rod can be provided with a section of higher stiffness, the possible indications can be substantially extended. Thus, a section of higher stiffness may be used for the fusion of vertebral bodies while a section of lower stiffness may be used for the elastic connection of a neighboring vertebral body.

Today, the "golden standard" in spinal surgery still consists in the fusion (stiffening) of pathologic vertebral bodies. However, fusions often lead to premature degeneration of the segments adjacent to the fusion. Therefore, attempts are being made to provide rods having different degrees of stiffness and to include neighboring segments in the surgical treatment.

The approaches of the prior art to solving this problem will be set forth below.

The invention according to patent application US 2008/0319486 discloses a connecting element having a variable stiffness along its longitudinal axis. The variable stiffness is limited to the sections between two anchoring elements and provides a different response to pressure only.

The invention according to EP 2 113 216 also provides different degrees of stiffness. The connection of the different materials is either achieved by interpenetration or by a butt joint. The material differences are limited to differences in hardness and in bending flexibility. Differences in longitudinal or transversal stiffness are not disclosed. The butt joints are designed for normal stresses exclusively.

The invention according to patent application US 2008/0177388 also connects different rod materials, but this is achieved according to the male/female principle, which is demanding with regard to the production technique.

The invention according to patent application US 2009/0248083 also provides sections of different stiffness, however with a varying core that is difficult to anchor particularly in the stiffer areas.

The invention according to patent application WO 97/32533 provides a varying stiffness due to a varying external diameter, thereby making the rod more difficult to anchor.

The invention according to patent application US 2008/0306536 aims to achieve a variable stiffness between vertebral bodies by connecting the connecting element to the bone screw with variable stiffness. This solution is space-consuming and may have unfavorable consequences for the patient.

The invention according to patent application WO 2007/038429 also allows achieving different degrees of stiffness due to a modular construction but, according to the claims, only in response to bending stresses and not to tensile and compression loads.

The invention according to patent application US 2005/0203513 also provides different degrees of stiffness in that for one part, the core inside a cylindrical wall varies or, for the other part, the stiffness of a connecting element is locally reduced by material removal. On one hand, this entails the difficulty of anchoring a core by means of a wall of a different kind, and on the other hand, the difficulty of sections of predetermined length, which in the case of multisegment treatments involves significant logistic complexity.

The invention according to patent application US 2007/0129729 also provides a stiff and an elastic rod portion whose connection is interpenetrating and is supported by a cable.

The invention according to patent application US 2006/0041259 provides a variable stiffness along its rod axis. The variation is achieved by a helical slot (or spiral slot) reflecting the mechanical principle of a spiral spring. The spring may also be filled with a core and such core may be secured to the spring by welding or bonding. The variation may further be achieved by assembling rods of different properties one behind the other. However, the patent application does not disclose any method of sequentially connecting one rod to the other. Nor does it disclose how the anchorage of the rod in a bone screw would interface with such a connection site.

The inventions according to the patent applications CH 702636 or US 2006/0095134 disclose only blunt connections (butt joint connections) or blunt transitions.

Thus it follows from the prior art that most connections are butt joints, at least peripherally, and thus extend in a plane parallel to the clamping plane in the screw head.

SUMMARY OF THE INVENTION

Accordingly, it is the object of the invention described hereinafter to provide a biocompatible plastic rod having at least two sections of different stiffness along its longitudinal axis.

This object is achieved in that rod segments having different degrees of stiffness are interconnected in a plane that is oblique to the longitudinal rod axis. The connection may be achieved by bonding or welding or by a combination of both. In the case of welding, especially heating techniques (e.g. plates or mirrors), motion techniques (e.g. vibration or ultrasonic welding), or a combination of both may be contemplated.

Such a rod of variable stiffness is defined in the claims. The claims define preferred embodiments. According to the claims, the plastic material may be a polycarbonate urethane.

In contrast to US 2006/0041259, the present invention discloses a connection of different rods along an inclined plane, in order to not only have normal loads across the connection site, i.e. perpendicular to the connection plane, but also shear loads. The present invention discloses rods with plain sections and connection areas extending over the entire cross section. The inclination angle of the inclined plane is determined in order to avoid an anchorage which clamps from two opposite sides across the connection plane.

Furthermore, it is avoided that a connecting plane coincides with a clamping plane and the connection, besides normal stresses, is also ensured by more suitable shear stresses.

BRIEF DESCRIPTION OF THE DRAWINGS

The present invention is explained in more detail hereinafter by way of preferred examples with reference to drawings which merely illustrate exemplary embodiments and in particular do not show the maximum number of different consecutive degrees of stiffness.

The Figures schematically show.

DESCRIPTION OF EMBODIMENTS

Figure 1A:
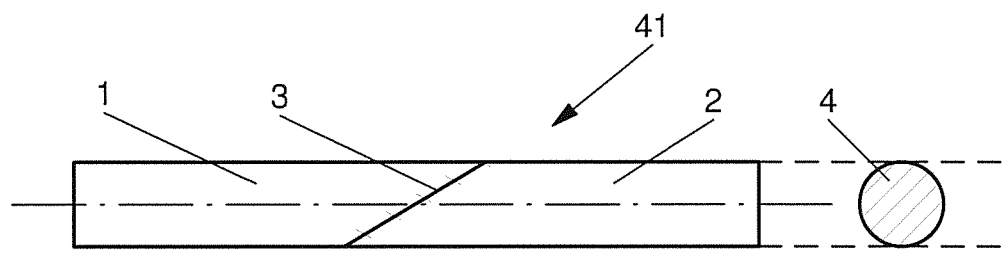
FIG. 1a: a point-symmetrical rod having sections of different degrees of stiffness connected via an oblique plane.

FIG. 1a shows a left 1 and a right 2 segment of a rod 41 having a point-symmetrical cross-section 4 and the oblique weld seam 3 connecting them.

Figure 1B:
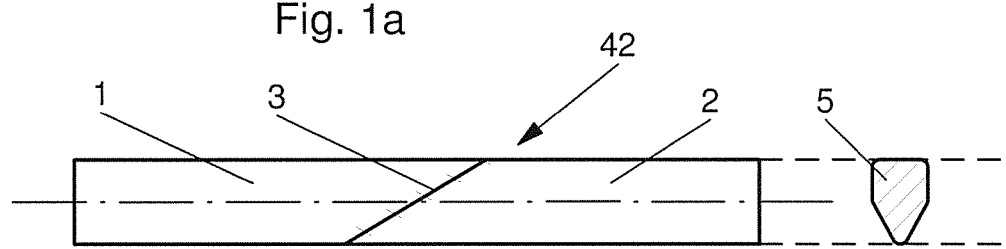
FIG. 1b: a rod having an arbitrary cross-section (e.g. with two plane-parallel sides) and sections of different degrees of stiffness connected via an oblique plane.

FIG. 1b shows a left 1 and a right 2 segment of a rod 42 having an arbitrary cross-section 5, e.g. with two plane-parallel sides, and the oblique weld seam 3 connecting them.

Figures 2A, 2B, 3A, 3B:
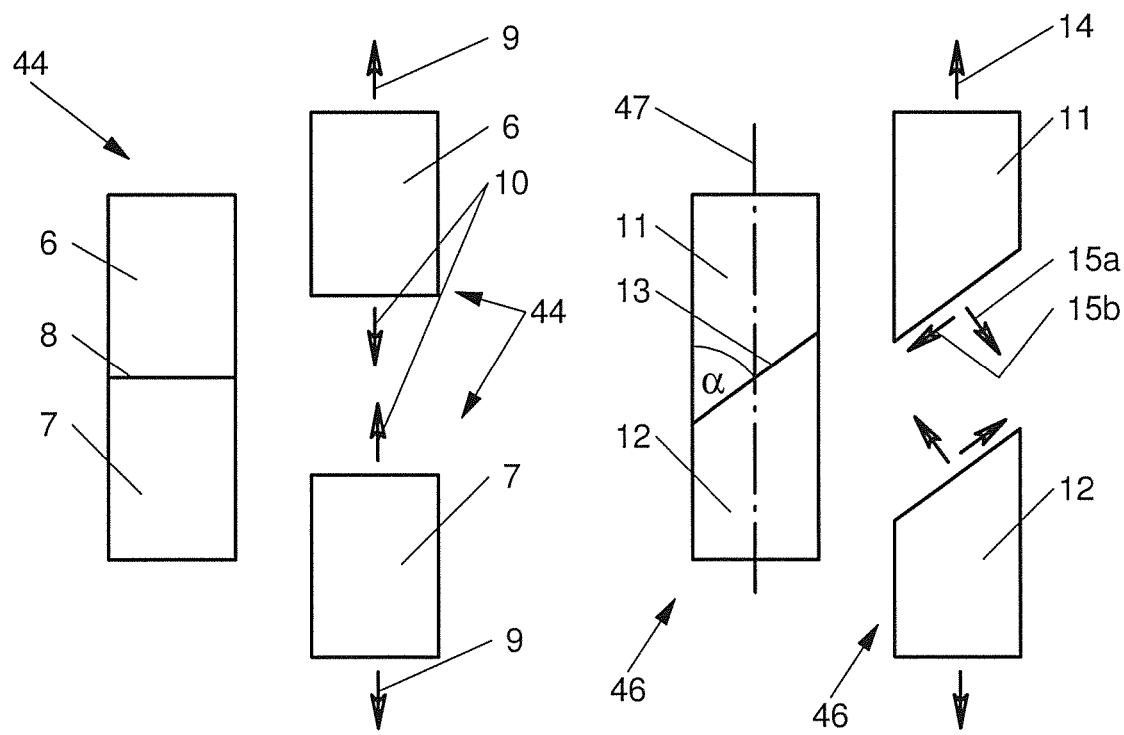
FIGS. 2a and 2b: the reaction forces for a rod connected by a butt-joint.
FIGS. 3a and 3b: the reaction forces for an oblique connection according to the invention and the angle α of the connecting plane.

FIGS. 2a and 2b show an upper 6 and a lower 7 segment of a rod 44 connected by a butt joint 8 according to the prior art. In FIG. 2b, arrow 9 represents the external force and arrow 10 the reaction force in a sectional view. Here the reaction force exclusively consists of a normal force according to arrow 10.

In contrast, FIGS. 3a and 3b show an upper 11 and a lower 12 segment of rod 46 interconnected by an oblique joint 13. In FIG. 3b, arrow 14 represents the external force and arrow 15 the reaction forces in a sectional view. Here the reaction forces consist of a normal force 15a and of a shear force 15b. The angle α denotes the angle between the plane of the joint 13 and the longitudinal axis 47 of rod 46, or, as illustrated, the side face of rod 46.

Figure 4:
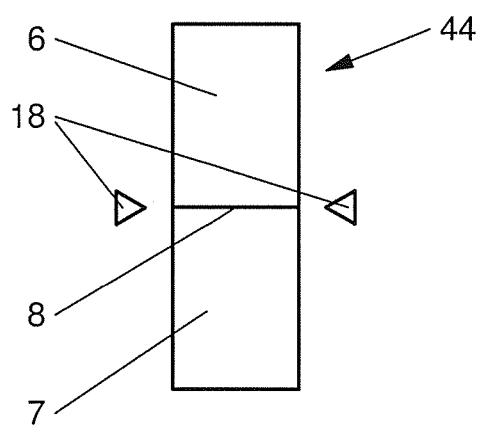
FIG. 4: clamping ridges on a butt joint.

FIG. 4 shows an upper 6 and a lower 7 segment of a rod 46 connected by a butt joint 8. If clamping ridges 18 apply on the connecting plane, they will apply a load to the weld seam of joint 8 from both sides.

Figure 5:
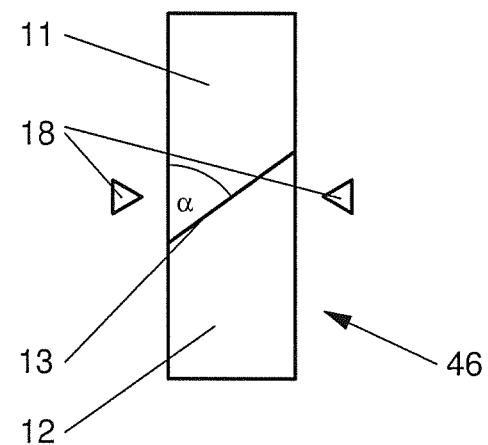
FIG. 5: clamping ridges on an oblique connection.

FIG. 5 shows an upper 11 and a lower 12 segment of an obliquely connected rod. Clamping ridges 18 apply on one side of the weld seam 13 at the most.

Consequently, the disclosed invention offers multiple advantages, as explained below.

An oblique connection 13 with an angle of inclination α between 5° and 85°, preferably 45°, always represents a larger surface than a connection that is perpendicular to the rod axis 47. In this manner, tensions in the connection are reduced. Furthermore, shear stresses result, which are generally more suitable for connections than normal stresses i.e. stress perpendicular to the connecting plane.

If a clamping device comprises ridges 18 located in one and the same clamping plane and if these ridges apply in a connecting plane 8 that is orthogonal to the rod axis, they will penetrate into the connecting plane from both clamping sides. In the case of a bonded joint or a weld seam, a critical splitting force may result.

If a clamping device comprises ridges 18 located in one and the same clamping plane and if these ridges apply to an oblique connecting plane 13, only one ridge 18 may apply a load to the connection on one clamping side, and no force is exerted on other sections of the connection plane 13. Moreover, the clamping does not act in the oblique connecting plane and thus has no direct splitting or cleaving effect either.

This connection method allows connecting rod segments with large differences in longitudinal or transversal stiffness. To this end, the rod segments have to be dry. In order to allow the subsequent clinical application of rod segments of high stiffness, these have to be rehydrated after their connection and delivered in a preferably saturated condition.

The description of the examples enables the one skilled in the art to perceive modifications and alternations without leaving the scope of protection defined by the claims.

What is claimed is:

1. A plastic connecting rod assembly for a surgical treatment of a spine, comprising a clamp having two opposed clamping ridges, and a plastic rod having at least two rod segments having different properties,
   wherein the at least two rod segments are interconnected at respective planar end faces thereof to form a connection,
   wherein said planar end faces lie along an oblique plane which is oblique with respect to a longitudinal axis of the plastic rod,
   wherein said two opposed clamping ridges are arranged in a clamping plane to engage opposite sides of the plastic rod;
   wherein an obliquity angle of said oblique plane is large enough so that at least one end of said oblique plane lies outside the clamping plane, the clamping plane being defined perpendicular to said longitudinal axis,
   wherein the oblique plane forms an angle in the range 45° to 85° with the longitudinal axis of the plastic rod.

2. The plastic connecting rod assembly according to claim 1, wherein the connection is welded.

3. The plastic connecting rod assembly according to claim 2, wherein the connection is vibration-welded.

4. The plastic connecting rod assembly according to claim 1, wherein the connection is bonded.

5. The plastic connecting rod assembly according to claim 1, wherein the connection is welded and bonded.

6. The plastic connecting rod assembly according to claim 1, wherein the at least two rod segments of the plastic rod are limited to two.

7. The plastic connecting rod assembly according to claim 1, wherein the plastic rod is made of a polycarbonate urethane.

8. The plastic connecting rod assembly according to claim 1, wherein the at least two rod segments are rehydrated to saturation after their connection.

9. The plastic connecting rod assembly according to claim 1, wherein the at least two rod segments have different stiffness properties, respectively.

10. The plastic connecting rod assembly according to claim 1, wherein the plastic rod has two ends and an outer surface defined between the two ends, and the at least two rod segments are interconnected at a line defined in the outer surface, and said line defines said oblique plane.

11. A method for producing a plastic connecting rod assembly for a surgical treatment of a spine, including a clamp having two opposed clamping ridges, and a plastic rod having at least two rod segments having different properties, the method comprising:
   interconnecting the at least two rod segments at respective planar end faces thereof to form a connection,
   wherein said planar end faces lie along an oblique plane which is oblique with respect to a longitudinal axis of the plastic rod,
   arranging said two opposed clamping ridges in a clamping plane to engage opposite sides of the plastic rod;
   providing an obliquity angle of said oblique plane that is large enough so that at least one end of said oblique plane lies outside the clamping plane, the clamping plane being defined perpendicular to said longitudinal axis,
   wherein the oblique plane forms an angle in the range 45° to 85° with the longitudinal axis of the plastic rod.

12. The method of claim 11, wherein the at least two rod segments are dried prior to being connected along the oblique plane and the plastic rod is then rehydrated.

13. The method of claim 11, wherein the at least two rod segments are rehydrated to saturation after their connection.

14. The method of claim 11, wherein the connection is welded.

15. The method of claim 14, wherein the connection is vibration-welded.

16. The method of claim 11, wherein the connection is bonded.

* * * * *